United States Patent [19]

Elfert et al.

[11] Patent Number: 4,628,207

[45] Date of Patent: Dec. 9, 1986

[54] SPECIAL ENDOSCOPE FOR VISUALLY TESTING FOR CRACKS

[75] Inventors: Bernd Elfert, Mülheim; Werner Schölly, Denzlingen, both of Fed. Rep. of Germany

[73] Assignee: Kraftwerk Union Aktiengesellschaft, Mülheim, Fed. Rep. of Germany

[21] Appl. No.: 717,576

[22] Filed: Mar. 29, 1985

[30] Foreign Application Priority Data

Apr. 3, 1984 [DE] Fed. Rep. of Germany ....... 3412434
Oct. 24, 1984 [DE] Fed. Rep. of Germany ....... 3438971

[51] Int. Cl.⁴ .............................................. G02B 23/26
[52] U.S. Cl. ............................. 250/461.1; 350/96.26; 356/241; 128/6
[58] Field of Search ........................ 128/664, 665, 6; 350/96.26, 96.15; 356/241; 250/301, 461.1, 302

[56] References Cited

U.S. PATENT DOCUMENTS

3,610,726 10/1971 Aijala ................................ 350/95.26
3,942,866 3/1976 Roman ............................... 350/95.26
4,272,156 6/1981 Ishibashi et al. .................. 350/95.26
4,273,110 6/1981 Groux .................................... 128/6
4,281,929 8/1981 Lord et al. ........................... 356/241

OTHER PUBLICATIONS

Thomas Schulz, "kleine Welt" Journal *Hobby Magazin der Technik* No. 4, Apr. 13, 1982, pp. 10, 11, 12 and 14.

*Primary Examiner*—Janice A. Howell
*Assistant Examiner*—Constantine Hannaher
*Attorney, Agent, or Firm*—Herbert L. Lerner; Laurence A. Greenberg

[57] ABSTRACT

A special endoscope for examining the structure of surfaces of measuring sites in narrow gaps formed in parts to be inspected includes a sword-shaped probe having an end, a narrow canal with a substantially uniform cross section disposed in the probe, at least one magnifying image-conducting optical system disposed in the canal having a receiving end face, image-illuminating optical systems disposed in the probe in the form of a plurality of optical waveguide strands having transmitting end faces at the end of the probe in immediate vicinity of the receiving end face, the transmitting end faces being grouped in the shape of a fan about the receiving end face for illuminating the measuring site, a UV light source connected to the image-illuminating optical systems for transmitting rays from the transmitting end faces and reflecting the rays off the surface structure in the visible frequency range onto the receiving end face, and means connected to the image-conducting optical system for producing a real image from the rays.

17 Claims, 13 Drawing Figures

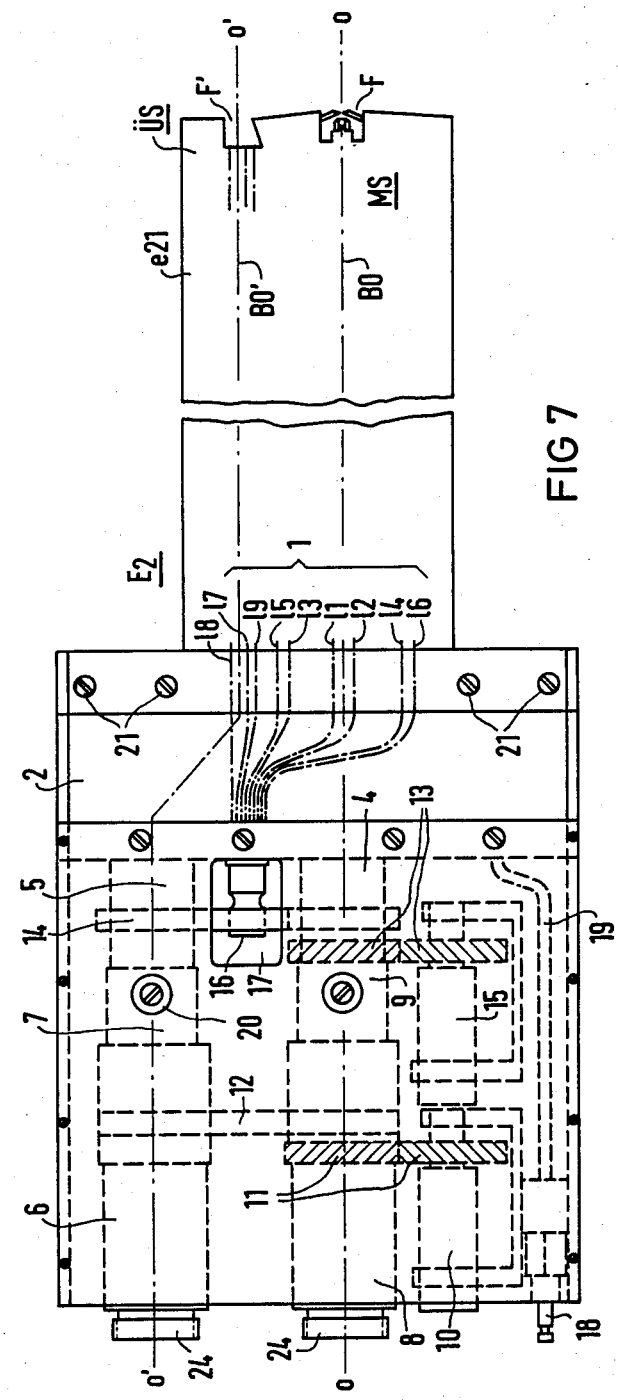
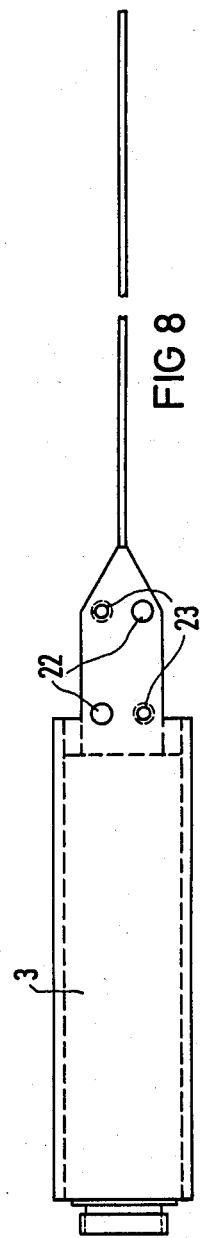
FIG 7
FIG 8

SPECIAL ENDOSCOPE FOR VISUALLY TESTING FOR CRACKS

The invention relates to a special endoscope for examining the surface structure in narrow gaps, especially for the visual testing of parts to be examined for cracks and possible growth of cracks, wherein the surface regions of the parts to be inspected are illuminated by means of light sources through image-illuminating optical systems, causing reflected light waves to generate a real image on observation and/or recording equipment through at least one image-conducting optical system in the form of lens and/or optical or light waveguide systems, and the surface regions to be inspected for cracks being cleaned and then wetted with a penetrating agent having fluorescent properties and being illuminated by means of UV light, reflecting the rays of the UV light at the penetrated surface structure in the visible frequency range.

The purpose of the invention is to overcome the problem of introducing such a special endoscope into narrow gaps and to nevertheless be able to guarantee good illumination and imaging conditions. One application is for the inspection of the end faces of the wheel discs of turbine rotors having a disc structure in vicinity of axial rotation-prevention pins. These wheel-disc regions are subjected to increased stresses during operation and must be examined at regular intervals for cracks that may be present. The width of the gap between a given wheel disc and the adjoining disc in many cases is only about 2 mm, and the special endoscope must be immersed to a depth of about 200 mm in order to reach the end face regions to be examined.

There have heretofore been no suitable solutions to this examination problem. Due to the crowded structural conditions, it has not been possible to bring the amount of UV light required for the crack inspection to the measuring site. It has therefore been necessary to loosen the shrink fit of the wheel discs and to disassemble them in order to carry out a visual inspection for incipient cracks.

It is accordingly an object of the invention to provide a special endoscope for visually testing for cracks, which overcomes the hereinafore-mentioned disadvantages of the heretofore-known devices of this general type, and which permits a visual inspection for cracks in very narrow gaps in the order of about 2 mm to be carried out and good illumination and imaging results to be obtained without expensive exposure of examination surfaces by disassembly of parts. A particular problem is the construction of a special endoscope which permits visual testing for cracks in the end faces of wheel discs of the disc rotors in steam turbines in the region of their axial rotation prevention devices.

With the foregoing and other objects in view there is provided, in accordance with the invention, a special endoscope for examining the structure of surfaces of measuring sites in narrow gaps formed in parts to be inspected, the surface having been wetted after cleaning with a penetrating agent having fluorescent properties for visual crack growth examination thereof, comprising a sword-shaped probe having an end, a narrow canal with a substantially uniform cross section disposed in the probe, at least one magnifying image-conducting optical system in the form of lens and/or light waveguide systems disposed in the canal having a receiving end face, image-illuminating optical systems disposed in the probe in the form of a plurality of optical waveguide strands having transmitting end faces at the end of the probe in immediate vicinity of the receiving end face, the transmitting end faces being grouped in the shape of a fan about the receiving end face for illuminating the measuring site, a UV light source connected to the image-illuminating optical systems for transmitting rays from the transmitting end faces and reflecting the rays off the surface structure in the visible frequency range onto the receiving end face, and means connected to the image-conducting optical system for producing a real image from the rays.

In accordance with another feature of the invention, the canal is in the form of one capillary disposed substantially along a center line of the probe, and including other capillaries in which the image-illuminating optical systems are disposed, an arched protective bracket defining an outer contour of the probe and surrounding the image-conducting optical system, the image-illuminating optical systems and the transmitting and receiving end faces, and a stiffening leaf interconnecting and mutally fixing the capillaries and the bracket in place.

In accordance with a further feature of the invention, there are provided other canals disposed in the probe for accomodating the optical waveguide strands, and plate halves each having a mutually congruent half of each of the canals formed therein with semicircular cross sections, the plate halves having recesses formed therein in vicinity of the end of the transmitting and receiving end faces, and the canal halves of the probe being joined together with the optical systems disposed therein.

In accordance with an added feature of the invention, the probe includes a relatively wider macroprobe part for the actual crack inspection having the image-conducting optical system disposed therein, and a relatively narrower adjoining survey probe part for orienting and positioning the macroprobe part, having an imaging factor $V_2$ within the limits $0.5 \leq V_2 < V_1$, where $V_1$ is the linear magnification of the macroprobe part.

In accordance with an additional feature of the invention, the image-conducting optical system has an optical axis, the receiving end face thereof receives rays in a given receiving area, the light or optical waveguide strands are in the form of a first group of image-illuminating optical systems including at least one optical waveguide strand disposed on each respective side of the optical axis immediately adjacent and axially parallel to the axis, and a second group of image-illuminating optical systems having the transmitting end faces thereof leading to the receiving area of the receiving end face of the image-conducting optical system, the second group including at least one optical waveguide strand disposed on each respective side of the optical axis at a distance from the optical waveguide strands of the first group, the optical waveguide strands of the second group having an end region with a radius of curvature curving toward the receiving area of the image-conducting optical system, and the transmitting end faces of the optical waveguide strands of the second group illuminating the measuring site adjacent the transmitting end faces of the optical waveguide strands of the first group.

In accordance with again another feature of the invention, the first group includes a pair of image-illuminating optical systems disposed on each respective side of the image-conducting optical system and parallel to the optical axis.

In accordance with again a further feature of the invention, the second group includes a pair of image-illuminating optical systems disposed on each respective side of the image-conducting optical system.

In accordance with again an added feature of the invention, the recess is a stepped marginal recess having lateral surfaces, the first-mentioned canal for the image-conducting optical system projects a given distance into the recess, the other canals for the optical waveguide strands of the first group project less than the given distance into the recess, and the other canals for the optical waveguide strands of the second group open into the lateral surfaces of the recess.

In accordance with again an additional feature of the invention, the survey probe part includes an optical axis, an image-conducting optical system, and at least one image-illuminating optical system disposed on each respective side thereof and parallel to the optical axis.

In accordance with yet another feature of the invention, the survey probe part includes a double strand of image-illuminating optical systems on a longitudinal side thereof facing the macroprobe part.

In accordance with yet a further feature of the invention, the survey probe part includes an image-conducting optical system with a receiving end face receiving rays in a given receiving area, some of the canals are formed in the plate halves in the macroprobe part and some in the survey probe part adjacent the canals formed in the macroprobe part, and the plate halves have a marginal recess formed therein at the receiving area in which the receiving and transmitting end faces are disposed.

In accordance with yet an added feature of the invention, the canals include empty canals disposed at least in the macroprobe part, and, if applicable, in the survey probe part, the empty canals being feed canals for blocking air forming an air veil during flushing and cleaning of the measuring site to be examined for protection against contamination of the optical systems in vicinity of the recess and optionally for the protection of the optical systems of the survey probe part.

In accordance with a concomitant feature of the invention, the image-producing means are in the form of observation and/or recording equipment.

The advantage achievable through the use of the invention are in particular the following: examination with a special endoscope according to the invention represents a supplement to an ultrasonic test. It can be carried out with relatively little equipment and permits a direct statement regarding the location, form and radial extent of a defect.

Other features which are considered to be characteristic for the invention are set forth in the appended claims.

Although the invention is illustrated and described herein as embodied in a special endoscope for visually testing for cracks, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 7 is a top-plan view, in phantom, showing an adapter box of the special endoscope on the eye-piece side, the interior of which contains, among other things, two adjustable TV adapters for the macro and the survey probe part, as well as a light waveguide connection for coupling-in UV radiation, a wedge-shaped sword carrier extension and a shortened sword-shaped probe itself;

FIG. 8 is a fragmentary, side-elevational view of the device according to FIG. 7;

Figure 11:
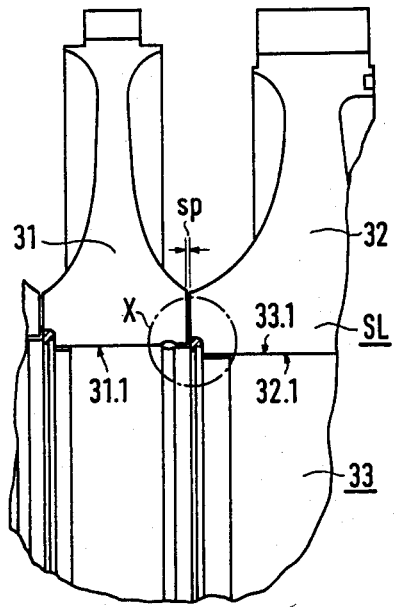
FIG. 11 is an enlarged, fragmentary, elevational view showing the details of two adjacent wheel discs, shrunk on a shaft of a low-pressure rotor of a steam turbine, wherein the end faces of the wheel discs facing each other are to be examined in the region X and in the region of the axial rotation-prevention pins, with respect to the surface structure thereof.
Figure 13:
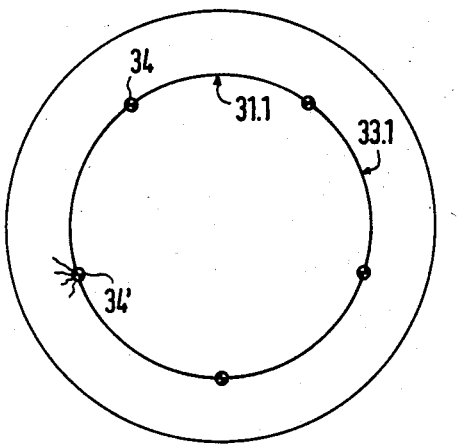
Figure 12:
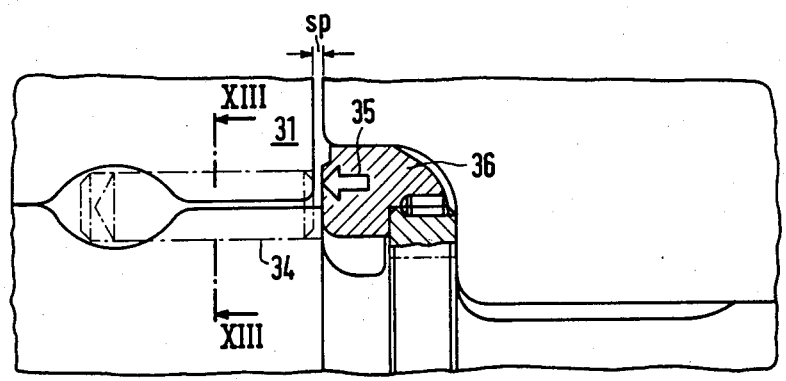

FIG. 12 is an enlarged view of the region X of FIG. 11, wherein an individual axial rotation-prevention pin is indicated with its contours in dot-dash lines; and FIG. 13 is a cross-sectional view taken along the line XIII—XIII in FIG. 12 in the direction of the arrows, on an enlarged scale and as seen over the entire periphery, over which five axial rotation-prevention pins are distributed and indicated in the adjacent wheel disc region for an incipient crack.

In the field of medicine, an endoscope is understood to be a mirror instrument for examining body cavities. Endoscopes permit direct viewing of the organs (endoscopy) and the diagnosis of illnesses in individual cases, which remain unrecognized by clinical, laboratory or X-ray examination. However, in the meantime, endoscopes have found wide acceptance not only in medical technology but in technology quite generally.

Figure 1:
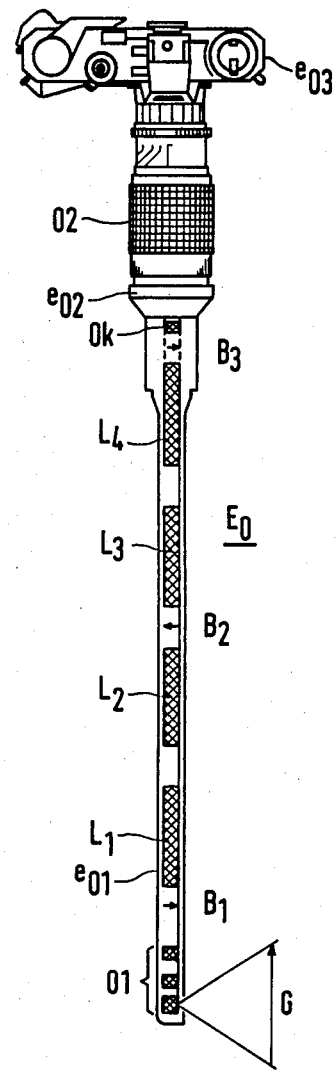
FIG. 1 is a diagrammatic, elevational view of a conventional endoscope with a mirror reflex camera attached to the end of the eye piece.

Referring now to the figures of the drawings in detail and first particularly to FIG. 1 thereof, there are seen optical relationships in an endoscope $E_O$, such as is used for magnified viewing and picture taking of models, such as landscaping and construction plans for which models are available (in this connection, reference should also be made to the Journal "Hobby Magazin der Technik" No. 4, Apr. 13, 1982, pages 10, 11, 12 and 14).

An objective lens 01 at the lower end of an endoscope shaft $e_{01}$ generates an image of an object G at a location $B_1$, wherein the deflection of the object rays incident from the side in the direction of the longitudinal axis of the endoscope shaft is accomplished by a suitable prism/lens system. The image at the location $B_1$ is produced by an optical system of rod lenses $L_1$ and $L_2$ producing an image at a location $B_2$. The image at the location $B_2$ is interchanged with respect to height and side relative to the image at the location $B_1$, which is why the lenses $L_1$ and $L_2$ are also called a "reverse system". A further reversal system $L_3/L_4$ images the image at the location $B_2$ at a location $B_3$. The image at the location $B_3$ can then be viewed with an eye piece Ok or photographed with a camera. A mirror reflex camera $e_{03}$ is mounted at an endoscope extension $e_{02}$. However, TV cameras can also be mounted to the endoscope extension $e_{02}$ with suitable adapters. In this prior art endoscope, the light for illuminating the models is supplied either by a built-in non-illustrated fiberglass line or by studio reflectors.

However, this conventional endoscope is not suited for examining the surface structure in narrow gaps. On the other hand, the invention relates to a special endoscope for examining the surface structure in narrow gaps, wherein gap widths down to 2 mm and even smaller can occur. The special problem in this case is firstly to introduce and to position the probe of the special endoscope in this narrow gap, and secondly to generate the required illumination in the narrow gap.

Figure 2:
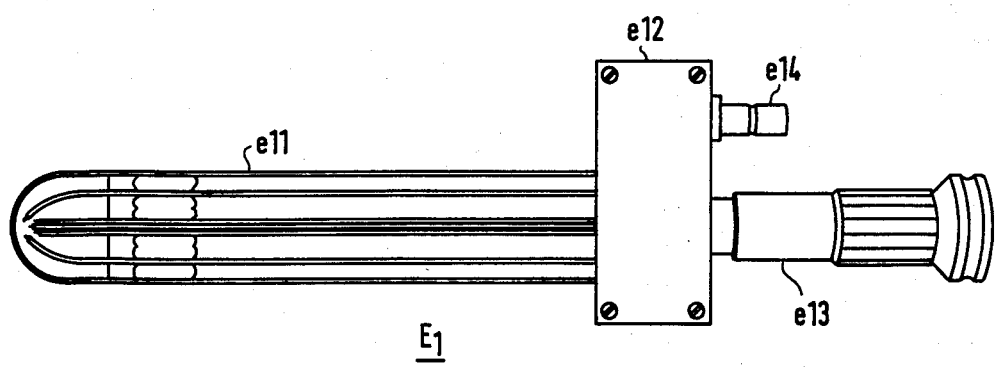
FIG. 2 is a top-plan view of a first embodiment of a special endoscope according to the invention, having a sword-shaped probe part with a capillary structure.
Figure 3:
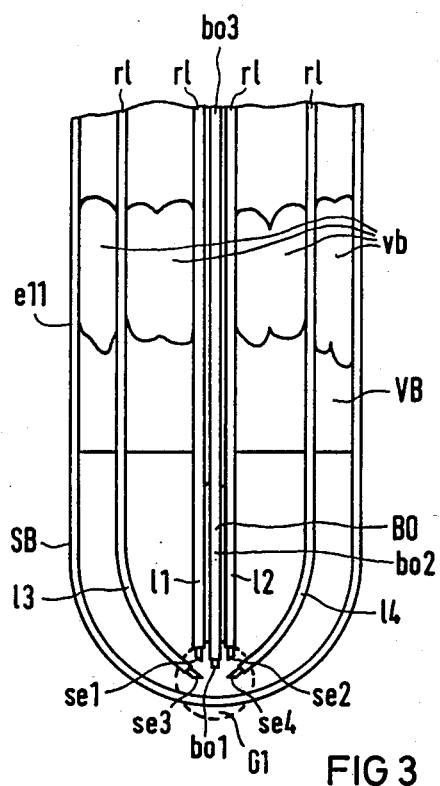
FIG. 3 is an enlarged fragmentary, top-plan view of the probe tip of the special endoscope according to FIG. 2.

FIGS. 2 and 3 illustrate a first embodiment of such a special endoscope $E_1$, formed of a sword-shaped probe e11, an eye piece e13, a terminal box e12 supporting the probe e11 and the eye piece e13, and a connecting point e14 on the box e11 for a non-illustrated light waveguide cable. As mentioned above, the special endoscope $E_1$ serves for examining the surface structure in narrow or very narrow gaps. The surface areas of the part to be inspected are illuminated by means of light sources through image-illuminating optical systems or light wave strands 11 to 14 shown in FIG. 3. The light waves are reflected by a surface area G1 to be examined which is indicated by broken lines. The reflected light waves generate a real image at an observation device (the eye piece e13) and/or a recording device (i.e. a photographic camera $e_{03}$ according to FIG. 1 or TV camera), through at least one image-transmitting optical system BO in the form of lens and/or light waveguide systems. In a special case of examination for cracks, i.e., in the case of visual testing for cracks of parts to be examined for a possible growth of cracks, the surface areas to be inspected are cleaned and then wetted with penetration agent having fluorescent properties and are illuminated by means of UV light. The UV light rays reflected at the penetrated surface structure G1 lie in the visible frequency range. The special endoscope shown in FIGS. 2 and 3 preferably serves for such a visual crack examination in gaps which have a gap width down to 2 mm or even less.

According to the invention, transmitting end faces se1, se2, se3, se4 of the light waveguide strands 11 to 14 are disposed in immediate vicinity of the receiving end face b01 of at least one magnifying, image-transmitting optical system BO accomodated in a narrow canal b02 having a uniform cross section. The strands illuminate the surface area or measuring site G1 and are grouped about the receiving end face b01 in fan-fashion at the end of the sword-shaped probe e11. This is done in such a manner that the UV light or the light from the transmitting end faces se1 to se4 generally, is projected to the measuring site G1 and from there to the receiving end face b01 as visible reflected light.

In the special endoscope $E_1$ according to FIGS. 2 and 3, the canal b02 for the image-conducting optical system BO is formed by a capillary b03, and the light waveguide strands 11 to 14 of the image-illuminating optical systems are also accomodated in capillaries r1. The capillary b03 of the image-conducting optical system BO is disposed on the center line or approximately on the center line of the sword-shaped probe e11, and the capillaries b03 and r1 of the image-conducting optical system BO and the image-illuminating optical systems or the corresponding light waveguide strands 11 to 14, respectively, including their transmitting and receiving end faces b01, se1 to se4 are surrounded by an arched protective bracket SB which defines the outer contour of the sword. The capillaries r1 of the optical waveguide strands 11 to 14 and the capillary b03 of the image-conducting optical system BO are connected to each other by a stiffening leaf VB and are fixed in their mutual relationship. In the embodiment example shown, soldering joints vb are distributed over the length of the sword-shaped probe e11. The joints vb are connected to the stiffening leaf which is formed of a solderable piece of sheet metal, such as Cu or brass, to the individual capillaries r1, b03. Therefore, the capillaries are also formed of a solderable material, for instance, copper. The structure of the special endoscope $E_1$ is so simple that it can be made in the laboratory.

Figure 4:
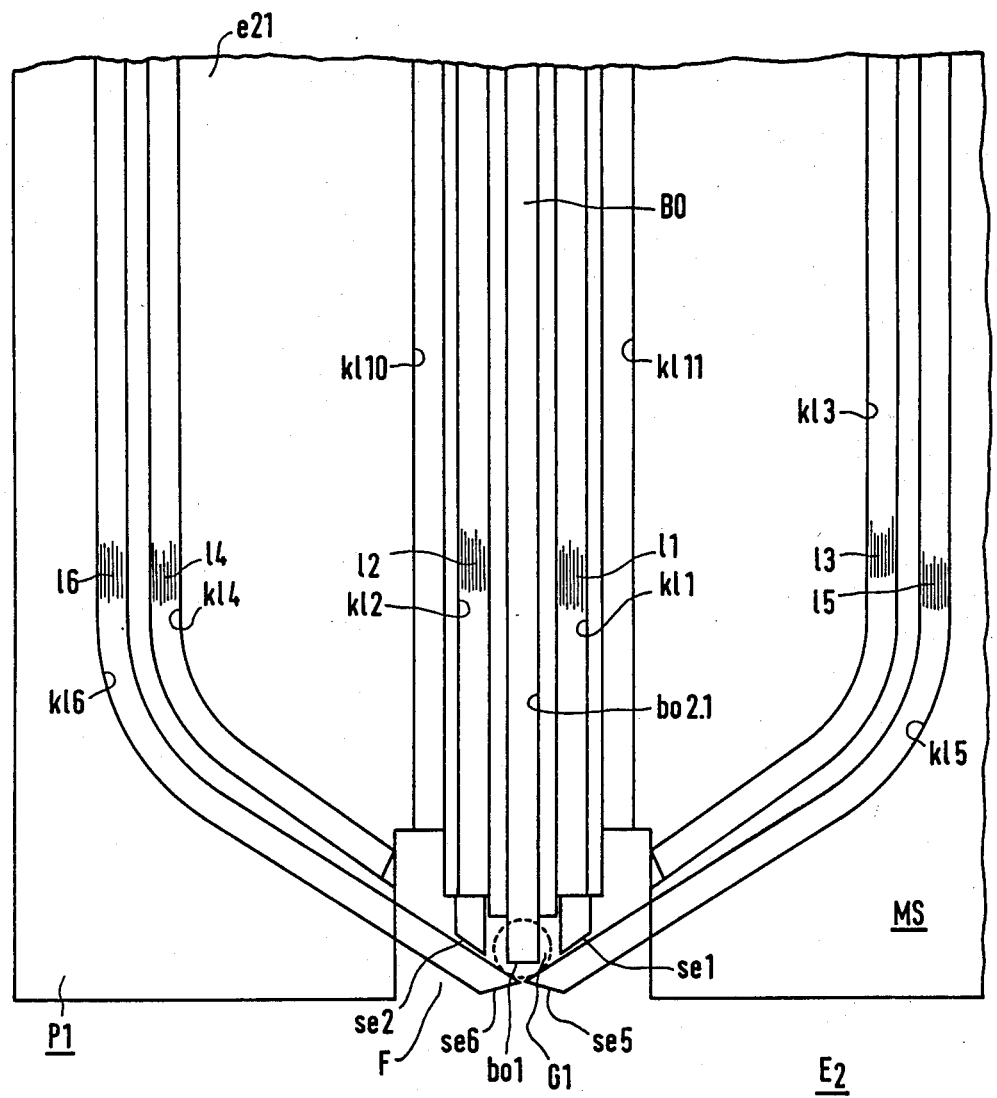
FIG. 4 is a further enlarged, fragmentary, top-plan view of the probe tip of a second embodiment of the special endoscope, in which the sword-like probe is formed of plate parts.

The second embodiment of a special endoscope $E_2$ is suitable for production in quantity and furthermore has the advantage of unambiguously defining the canals for the image-conducting and image-illuminating optical system without requiring great effort for adjustment. This construction will first be explained with the aid of FIGS. 4 to 6. It is seen that a canal b02.1 for the image conducting optical system BO and canals for optical waveguide strands 11 to 16 of the image-illuminating optical system, are mutually congruently formed into a plate half P1 (and logically in a second non-illustrated plate half which is coincident with the plate half P1) as canal halves k11 to k16. FIG. 4 shows a macro probe part MS, and more specifically, one folded plate half with the worked-in canals k11 to k16 for the optical waveguide strands 11 to 16, the strands only being shown diagrammatically at their ends and in section. Furthermore, two supply canals k110, k111 can be seen in FIG. 4. The canals k110 and k111 can be equipped with additional optical waveguide strands (which would logically have to be designated with reference numerals 110 and 111) in case still greater illumination is desired. In the center of or centered with, this macro probe part MS according to FIG. 4, the image-conducting optical system BO is inserted into the canal B02.1. The receiving end face b01 at the end of the optical system BO is in the form of a prism, so that the image-conducting optical system is aligned with the surface structure located laterally of the sword-shaped probe e11 or is aligned with the corresponding image spot or measuring site G1. Accordingly, the transmitting end faces se1 to se6 of the light-conducting strands 11 to 16 are also angled off, taking the index of refraction relative to the longitudinal axis of the optical waveguide strands into consideration. The angling off is formed in such a manner that the light rays emitted thereby are aligned with the image spot while being as free of losses as possible, and are then reflected by the image spot to the transmitting-receiving surface b01.

Figure 5:
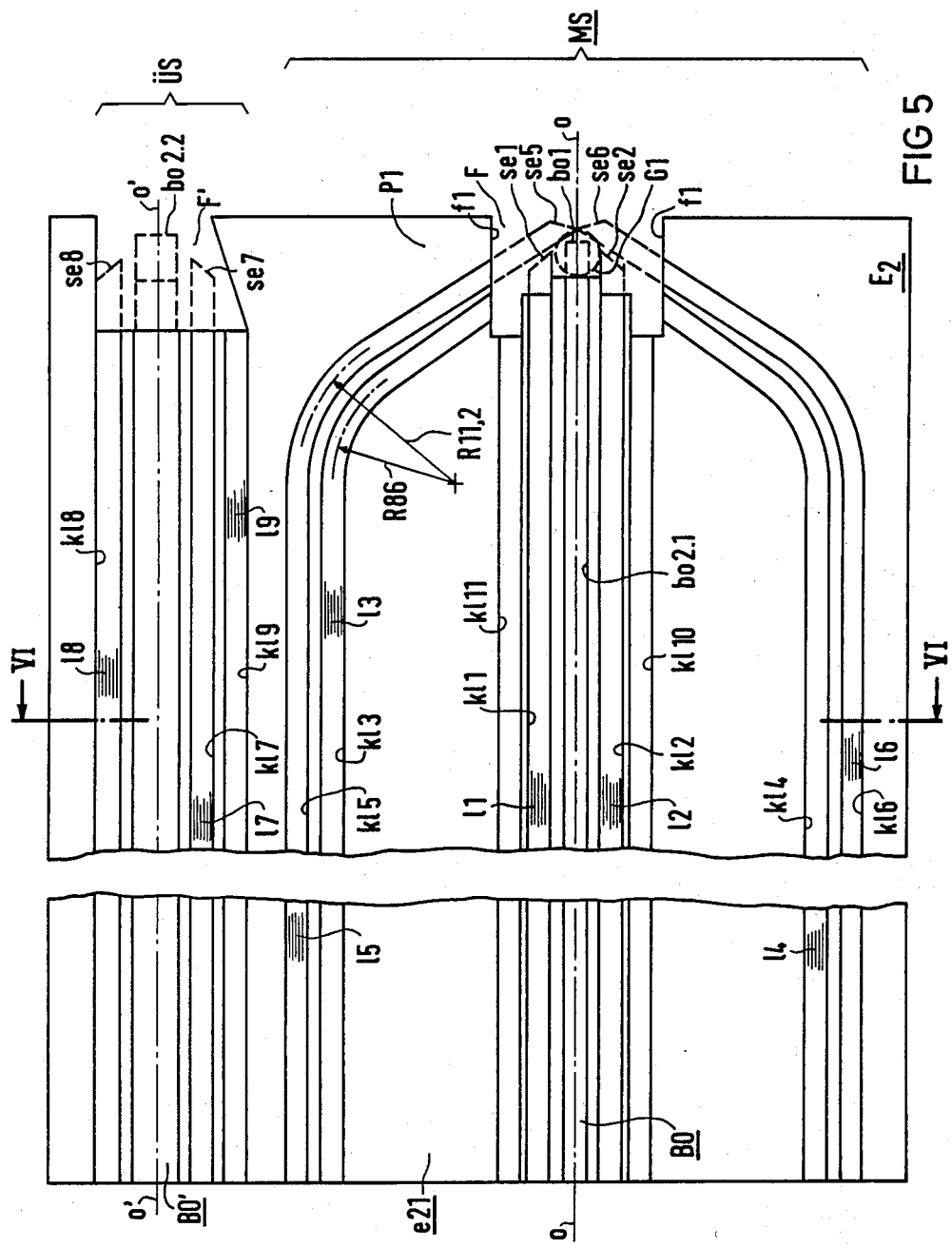
FIG. 5 is another fragmentary, top-plan view of the endoscope according to FIG. 4 on a slightly reduced scale, including a survey probe part besides the wider macro-probe part.

The plate half P1 (and the other non-illustrated congruent plate half P2) are recessed in vicinity of the ends and the transmitting and receiving end faces se1 to se6, the end face b01 of the image-illuminating optical systems 11 to 16 and the image-conducting optical system BO, in a manner shown in FIGS. 4 and 5, forming a marginal recess F.

Figure 6:
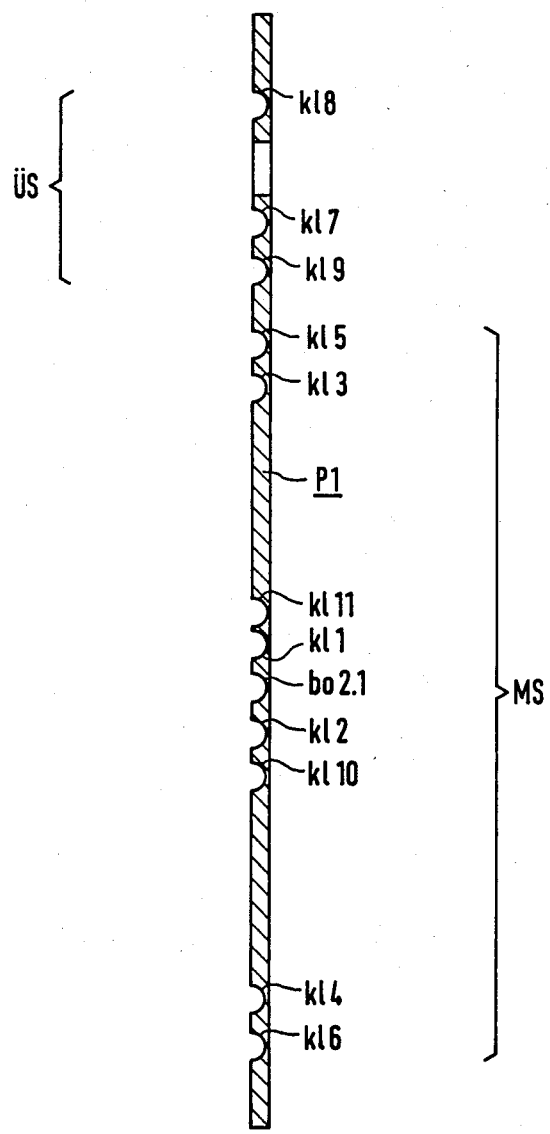
FIG. 6 is a cross-sectional view taken along the line VI—VI in FIG. 5 in the direction of the arrows, showing one plate half of the sword-like probe with worked-in canal halves for optical wave guides and optical systems conducting the image.

As is shown in FIG. 5 in conjunction with FIG. 6, a sword-shaped probe e21 which was formed by equipping one plate half P1 (or P2, respectively) with the image-conducting and image-Illuminating optical systems and by joining the two plate halves P1, P2, has a wider macroprobe part MS with the magnifying image-conducting optical system BO for the crack inspection proper and has an adjacent survey probe part ÜS. The survey probe part serves for the orientation and the positioning of the macroprobe part MS. The imaging factor $V_2$ thereof is within the limits between 0.5 and $V_1$, where $V_1$ is the linear magnification of the macroprobe part MS. The image-conducting optical system of the survey probe part ÜS is designated with reference symbol BO'; the image-illuminating optical systems thereof are again formed by optical waveguide strands, in this case the optical waveguide strands 17 to 19. The end of the optical waveguide strand 19 is not shown for the sake of greater clarity.

The canals for the image-illuminating optical systems can be produced in the plate halves P1, P2 by precision casting or by precision chip-removing processes such as milling, grinding, or electro-erosion.

As is shown in FIG. 5 and 6, the disposition of these canals on both sides of the optical axis 0—0 of the magnifying image-conducting optical system of the macroprobe part MS, is of a special nature. At least one optical waveguide strand 11, 12 each, of a first group of image-illuminating optical systems, is disposed immediately adjacent and parallel to the oprical axis 0—0 of the image-conducting optical system BO. A second group of image-illuminating optical systems 15, 16 with their transmitting end faces se5, se6, also open into the receiving area of the receiving end face B01 of the image-conducting optical system BO. This second group includes at least two further optical waveguide strands 15, 16, each of which is disposed on one side of the optical axis 0—0 of the image-conducting optical system BO, at a distance from the optical waveguide strands 11, 12 of the first group of image-illuminating optical systems. The end region of the systems 15, 16 are formed with a radius of curvature R 11.2 in the direction toward the receiving area b01 of the image-conducting optical system BO, in such a manner that its transmitting end faces se5, se6 adjacent the transmitting end faces se1, se2 of the first group of image-illuminating optical systems 11, 12, illuminates the measuring site G1. As illustrated in FIGS. 4 and 5, this second group of image-illuminating optical systems includes a total of four optical waveguide strands 13 to 16. A pair 13 to 15 and 14 to 16 of the strands is always installed on a respective longitudinal side of the image-conducting optical system BO. The ends of the optical waveguide strands 13 and 14 are not shown in vicinity of the window or recess F, in order to maintain the clarity of presentation. As already mentioned, only the two canals k11 and k12 are disposed in the first group of the image-illuminating optical systems. If required, the canals k110 and k111 can contain further optical waveguide strands as supply canals. However, they advantageously serve as blocking air canals which generate an air veil for protection against contamination of the optical systems BO, b01; se1, se2, etc. in vicinity of the window F, during a flushing and cleaning operation for the surface area to be examined. A corresponding empty canal serving for the conduction of the air may also be provided in the survey probe part ÜS.

FIGS. 5 and 6 also show that in addition to its centered image-conducting optical system BO', the survey probe part ÜS includes at least one image-illuminating optical system 17, 18, on each side of the image-conducting optical system BO', parallel to the optical axis o'—o' of the image-conducting optical system BO'. However, for even better illumination of the measurement site, a double strand of image-illuminating optical systems 17 and 19 is disposed on the longitudinal side of the survey probe part ÜS facing the macroprobe part MS. The canal fields of the macroprobe part MS and the survey probe part ÜS extend axially-parallel to each other within the plate half P1 (and the non-illustrated plate half P2), except for the radii of curvature 11.2 of the canals k15 and k16 and except for radii of curvature R86 of the canals K13 and k14. However, for better utilization of space, the curved canal parts again run parallel to each other and open into the marginal recess F, like the straight canal parts.

This recess F is in the form of a stepped marginal recess in vicinity of the ends and the transmitting and receiving end faces se1 to se6; b01 of the image-illuminating optical systems 11 to 16 and the image-conducting optical system BO. The plate canal b02.1 for the image-conducting optical system BO projects the farthest, the plate canals of the first group of image-illuminating optical systems 11, 12 are set back relative thereto, and the plate canals of the second group of image-illuminating optical systems 13, 15 and 14, 16 open at respectively angled lateral flanks or surfaces f1 of the marginal recess F.

The plate region of the survey probe part ÜS can also be provided with a marginal recess F' in the receiving region of its image-conducting optical system BO', within which the receiving and transmitting end faces se8, se9; b02.2 of its image-conducting optical systems 18, 17 (and similarly the end face se9 of the system 19) as well as its image-illuminating optical system BO' are disposed.

FIGS. 7 and 8 show the overall structure of the special endoscope with its sword-shaped probe e21 and the placement 1 of the waveguide strands (image-illuminating optical systems) which are fanned out to the individual canals 11 to 19, in dot-dash lines. Reference numeral 2 designates a sword holder which is bevelled toward the sword e21 on both sides and tapered with a 30° angle in wedge-fashion. Reference numeral 3 designates a connecting housing, in which the following items are accomodated:

a macroscope 4 with a focusing drive;
a survey endoscope 5 also having a focusing drive;

a TV adapter 6 with an image-size adjustment, including a plug-in coupling 7 leading to the survey endoscope 5;

a TV adapter 8 with an image-size adjustment and a plug-in coupling 9 leading to the macroscope 4;

a miniature motor 10 for driving the image-magnification and image-size adjustments; this involves, in particular, a 12-volt motor;

a gear drive 11 for image-magnification and image-size adjustment;

a serrated belt drive 12 for the image-size adjustment of the survey endoscope 5 (which can be retrofitted if required);

a gear drive 13 for adjusting the image focus and for focusing at the macroscope 4;

a serrated belt drive 14 for focusing at the survey encoscope 5 (which can be retrofitted if required);

a miniature motor 15 (12 volts) for driving the focusing system;

a light waveguide terminal 16 to which an external UV light waveguide cable can be connected through a non-illustrated plug-in coupling;

an operating well 17 for the light waveguide coupling;

an air connection coupling 18 with a valve;

an air line 19;

an operating well 20 for the plug-in coupling of TV adapters; and receiving threads 24 for non-illustrated TV cameras.

Reference numeral 21 in FIGS. 7 and 8 are fastening screws for the sword holder or base body 2 and the connecting housing reference numeral 22 designates holes for dowel pins; and reference numeral 23 designates fastening threads.

Elements 22 and 23 serve for fastening the special endoscope to a manipulator arm or the like.

The macroscope or the corresponding image-conducting optical system BO is focused along the axis o—o. The fine adjustment of the special endoscope with a manipulator or the like, in general serves for focusing the survey probe part ÜS. However, a separate focusing drive may also be provided as mentioned above. In the special endoscope E₂ shown, the light path of the image-conducting optical system BO' is deflected through prism systems in the survey probe part (see the bent optical axis o'—o').

Figure 9:
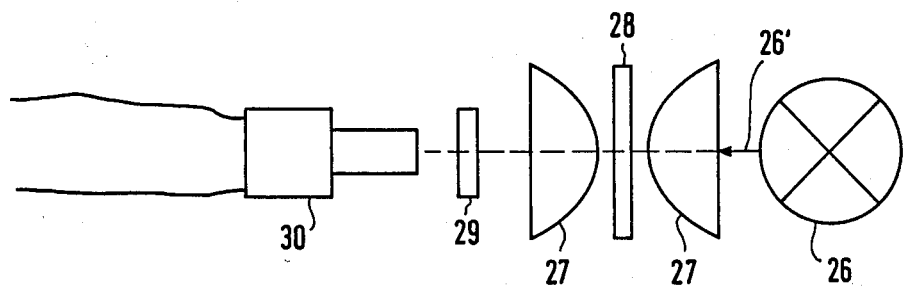
FIG. 9 is a schematic flow chart illustrating the principle of coupling a UV light source to the light waveguides.

FIG. 9 illustrates the principle of coupling an UV light source to a bundle of optical waveguides. A mercury high-pressure lamp 26 is provided with a spectral emission according to FIG. 10. UV light rays in a bundle 26' follow their path from the lamp 26 through the first of the two aspherical quartz lenses 27 which serve to concentrate light from the lamp 26 to the respective light waveguides. A special heat-protection filter 28 with a steep absorption edge, which passes the ultraviolet radiation unattenuated as far as possible and absorbs the infrared radiation as steeply as possible, is disposed between the two aspherical lenses 27. After passing through the second aspherical lens 37, the ray bundle 26' follows its path further, through a special interference filter 29 which serves the purpose of suppressing any radiation which is given off by the penetration agent excited by UV, but is no longer optimally received by the TV camera tube. Finally, the ray bundle 26' enters the light waveguide bundle 30.

Figure 10:
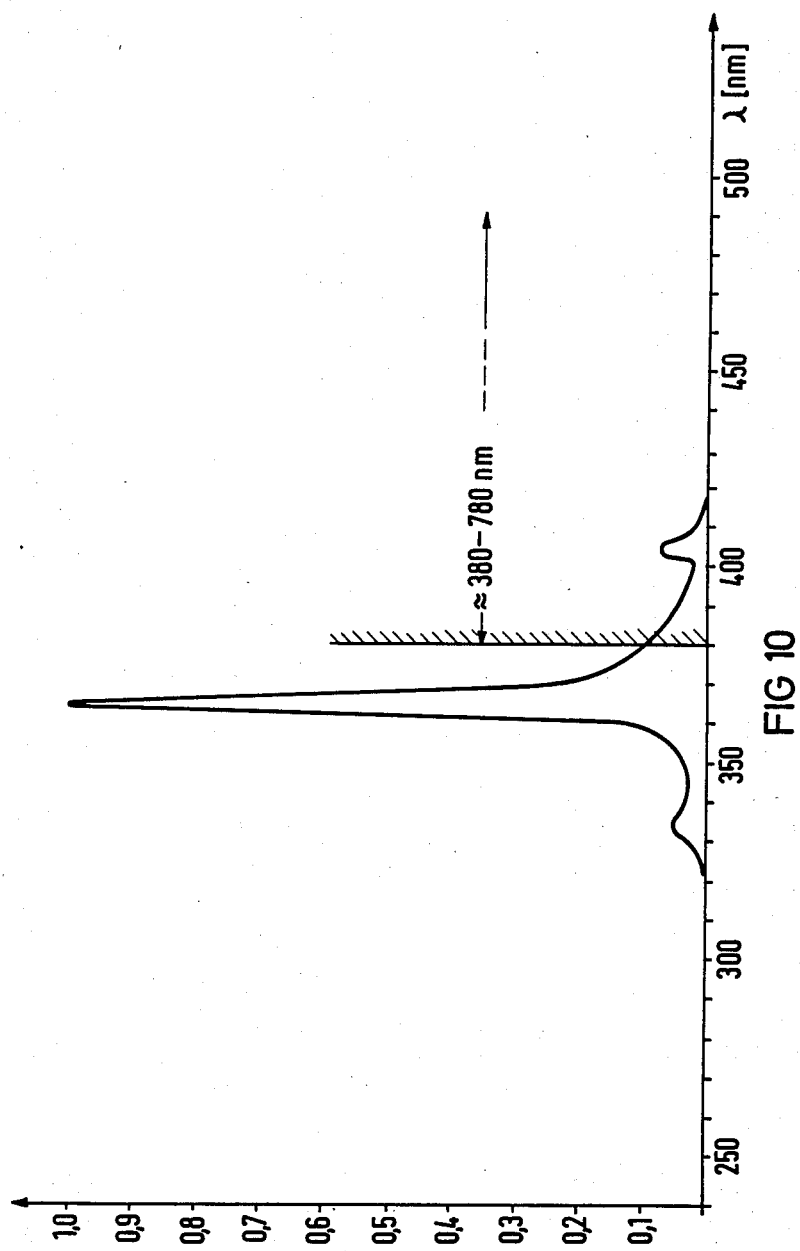
FIG. 10 is a graph of the curve of the spectral emission as a function of the wavelength plotted along the abscissa axis with a suitable mercury-vapor high-pressure lamp emitting in the UV range, the spectral emission being plotted on the ordinate axis in relative units and the wavelength on the abscissa axis in nm.

The mercury vapor high-pressure lamp which is used has a spectral emission with a pronounced maximum in the wave range between 360 and 370 nm, as shown in FIG. 10. The visible wavelength range which, as is well known, is between about 380 and 780 nm, is indicated in the diagram.

FIG. 11 shows a preferred field of application of the special endoscope for crack testing, in a disc rotor SL of a low-pressure turbine section of a turbo set, and two adjacent wheel discs 31, 32 being shown as an example. The inner peripheries 31.1, 32.1 of the hub parts of the wheel discs are each shrunk onto the outer periphery 33.1 of a shaft 33. In the region of the hub, an axial gap sp is provided between the adjacent wheel discs 31, 32 (or between the other wheel discs of the disc rotor). The special endoscope can be inserted with its sword-shaped probe through the gap into the region in which the possibility of crack formation due to stress corrosion in the region of the axial rotation-prevention devices or axial rotation-prevention pins, exists.

Such an axial rotation-prevention pin is indicated in the enlarged detailed area X and in FIG. 12 at reference numeral 34. The region of the wheel disc 31 at the end face marked by an arrow 35 (pin seating surfaces) can be inspected in particular through the gap sp with the special endoscope. The opposite region with the centering ring 36, however, is not subjected to material stress critical for cracks, so that to that extent an inspection is not necessary even if it were basically possible.

FIG. 13 further shows that five axial rotation protection devices 34 uniformly distributed over the circumference of the wheel disc seating surfaces are provided. At the point 34', the shape of a possible crack is indicated.

We claim:

1. Special endoscope for examining the structure of surfaces of measuring sites in narrow gaps formed in parts to be inspected, comprising a probe having an end, a narrow canal with a substantially uniform cross section disposed in said probe, at least one magnifying image-conducting optical system disposed in said canal having a receiving end face, image-illuminating optical systems disposed in said probe in the form of a plurality of optical waveguide strands having transmitting end faces at said end of said probe in immediate vicinity of said receiving end face, said transmitting end faces being grouped about said receiving end face for illuminating the measuring site, a UV light source connected to said image-illuminating optical systems for transmitting rays from said transmitting end faces and reflecting the rays off the surface structure in the visible frequency range onto said receiving end face, means connected to said image-conducting optical system for producing a real image from the rays, said canal being in the form of one capillary disposed substantially along a center line of said probe and other capillaries in which said image-illuminating optical systems are disposed, an arched protective bracket defining an outer contour of said probe and surrounding said image-conducting optical system, said image-illuminating optical systems and said transmitting and receiving end faces, and a stiffening leaf interconnecting and mutually fixing said capillaries and said bracket in place.

2. Special endoscope according to claim 1, wherein said image-producing means are in the form of observation equipment.

3. Special endoscope according to claim 1, wherein said image-producing means are in the form of recording equipment.

4. Special endoscope for examining the structure of surfaces of measuring sites in narrow gaps formed in parts to be inspected, comprising a probe having an end, a narrow canal with a substantially uniform cross section disposed in said probe, at least one magnifying image-conducting optical system disposed in said canal having a receiving end face, image-illuminating optical systems disposed in said probe in the form of a plurality of optical waveguide strands having transmitting end faces at said end of said probe in immediate vicinity of said receiving end face, said transmitting end faces being grouped about said receiving end face for illuminating the measuring site, a UV light source connected to said image-illuminating optical systems for transmitting rays from said transmitting end faces and reflecting the rays off the surface structure in the visible frequency range onto said receiving end face, means connected to said image-conducting optical system for producing a real image from the rays, other canals disposed on said probe for accomodating said optical waveguide strands, and plate halves each having a mutually congruent half of each of said canals formed therein with semicircular cross sections, said plate halves having recesses formed therein in vicinity of said transmitting and receiving end faces, and said canal halves of said probe being joined together with said optical systems disposed therein.

5. Special endoscope according to claim 4, wherein said probe includes a relatively wider macroprobe part having said image-conducting optical system disposed therein, and a relatively narrower adjoining survey probe part for orienting and positioning said macroprobe part, having an imaging factor $V_2$ within the limits $0.5 \leq V_2 < V_1$, where $V_1$ is the linear magnification of said macroprobe part.

6. Special endoscope according to claim 5, wherein said survey probe part includes an image-conducting optical system with a receiving end face receiving rays in a given receiving area, some of said canals are formed in said plate halves in said macroprobe part and some in said survey probe part adjacent said canals formed in said macroprobe part, and said plate halves have a marginal recess formed therein at said receiving area in which said receiving and transmitting end faces are disposed.

7. Special endoscope according to claim 5, wherein said canals include empty canals disposed at least in said macroprobe part, said empty canals being feed canals for blocking air forming an air veil during flushing and cleaning of the measuring site to be examined for protection against contamination of said optical systems in vicinity of said recess.

8. Special endoscope according to claim 5, wherein said canals include empty canals disposed at least in said macroprobe part, said empty canals being feed canals for blocking air forming an air veil during flushing and cleaning of the measuring site to be examined for protection against contamination of said optical systems in vicinity of said recess and for the protection of the optical systems of the survey probe part.

9. Special endoscope according to claim 4, wherein said recess is a stepped marginal recess having lateral surfaces, said first-mentioned canal for said image-conducting optical system projects a given distance into said recess, said other canals for said optical waveguide strands of said first group project less than said given distance into said recess, and said other canals for said optical waveguide strands of said second group open into said lateral surfaces of said recess.

10. Special endoscope for examining the structure of surfaces of measuring sites in narrow gaps formed in parts to be inspected, comprising a probe having an end, a narrow canal with a substantially uniform cross section disposed in said probe, at least one magnifying image-conducting optical system disposed in said canal having a receiving end face, image-illuminating optical systems disposed in said probe in the form of a plurality of optical waveguide strands having transmitting end faces at said end of said probe in immediate vicinity of said receiving end face, said transmitting end faces being grouped about said receiving end face for illuminating the measuring site, a UV light source connected to said image-illuminating optical systems for transmitting rays from said transmitting end faces and reflecting the rays off the surface structure in the visible frequency range onto said receiving end face, means connected to said image-conducting optical system for producing a real image from the rays, said probe including a relatively wider macroprobe part having said image-conducting optical system disposed therein, and a relatively narrower adjoining survey probe part for orienting and positioning said macroprobe part, having an imaging factor $V_2$ within the limits $0.5 \leq V_2 < V_1$, where $V_1$ is the linear magnification of said macroprobe part.

11. Special endoscope according to claim 10, wherein said survey probe part includes an optical axis, an image-conducting optical system, and at least one image-illuminating optical system disposed on each respective side thereof and parallel to said optical axis.

12. Special endoscope according to claim 11, wherein said survey probe part includes a double strand of image-illuminating optical systems on a side thereof facing said macroprobe part.

13. Special endoscope for examining the structure of surfaces of measuring sites in narrow gaps formed in parts to be inspected, comprising a probe having an end, a narrow canal with a substantially uniform cross section disposed in said probe, at least one magnifying image-conducting optical system disposed in said canal having a receiving end face, image-illuminiating optical systems disposed in said probe in the form of a plurality of optical waveguide strands having transmitting end faces at said end of said probe in immediate vicinity of said receiving end face, said transmitting end faces being grouped about said receiving end face for illuminating the measuring site, a UV light source connected to said image-illuminating optical systems for transmitting rays from said transmitting end faces and reflecting the rays off the surface structure in the visible frequency range onto said receiving end face, means connected to said image-conducting optical system for producing a real image from the rays, said image-conducting optical system having an optical axis, said receiving end face thereof receiving rays in a given receiving area, said optical waveguide strands being in the form of a first group of image-illuminating optical systems including at least one optical waveguide strand disposed on each respective side of said optical axis immediately adjacent and parallel to said axis, and a second group of image-illuminating optical systems having said transmitting end faces thereof in said receiving area of said receiving end face of said image-conducting optical system, said second group including at least one optical waveguide strand disposed on each respective side of said optical axis at a distance from said optical waveguide strands of said first group, said optical waveguide strands of said second group having an end region with a radius of curvature curving toward said receiving area of said image-conducting optical system, and said transmitting end faces of said optical waveguide strands of said second group illuminating the measuring site adjacent said transmitting end faces of said optical waveguide strands of said first group.

14. Special endoscope according to claim 13, wherein said first group includes a pair of image-illuminating optical systems disposed on each respective side of said image-conducting optical system and parallel to said optical axis.

15. Special endoscope according to claim 14, wherein said second group includes a pair of image-illuminating optical systems disposed on each respective side of said image-conducting optical system.

16. Special endoscope according to claim 13, wherein said second group includes a pair of image-illuminating optical systems disposed on each respective side of said image-conducting optical system.

17. Special endoscope for examining the structure of surfaces of measuring sites in narrow gaps formed in parts to be inspected, the surface having been wetted with a penetrating agent having fluorescent properties for crack examination thereof, comprising a probe having an end, a narrow canal with a substantially uniform cross section disposed in said probe, at least one magnifying image-conducting optical system disposed in said canal having a receiving end face, image-illuminating optical systems disposed in said probe in the form of a plurality of optical waveguide strands having transmitting end faces at said end of said probe in immediate vicinity of said receiving end face, said transmitting end faces being grouped about said receiving end face for illuminating the measuring site, a UV light source connected to said image-illuminating optical systems for transmitting rays from said transmitting end faces and reflecting the rays off the surface structure in the visible frequency range onto said receiving end face, means connected to said image-conducting optical system for producing a real image from the rays, said canal being in the form of one capillary disposed substantially along a center line of said probe and other capillaries in which said image-illuminating optical systems are disposed, an arched protective bracket defining an outer contour of said probe and surrounding said image-conducting optical system, said image-illuminating optical systems and said transmitting and receiving end faces, and a stiffening leaf interconnecting and mutually fixing said capillaries and said bracket in place.

* * * * *